US010300506B2

(12) United States Patent
Hiemer et al.

(10) Patent No.: US 10,300,506 B2
(45) Date of Patent: May 28, 2019

(54) DISPENSING APPARATUS, DISPENSING SYSTEM AND METHOD OF DISPENSING

(71) Applicant: Sulzer Mixpac AG, Haag (CH)

(72) Inventors: Andreas Hiemer, Rebstein (CH); Marco Zünd, Widnau (CH)

(73) Assignee: SULZER MIXPAC AG, Haag (CH)

( * ) Notice: Subject to any disclaimer, the term of this patent is extended or adjusted under 35 U.S.C. 154(b) by 0 days.

(21) Appl. No.: 15/324,354

(22) PCT Filed: Jul. 7, 2015

(86) PCT No.: PCT/EP2015/065466
§ 371 (c)(1),
(2) Date: Jan. 6, 2017

(87) PCT Pub. No.: WO2016/005383
PCT Pub. Date: Jan. 14, 2016

(65) Prior Publication Data
US 2017/0182511 A1    Jun. 29, 2017

(30) Foreign Application Priority Data

Jul. 9, 2014  (EP) ..................................... 14176325

(51) Int. Cl.
*B05C 17/005*    (2006.01)
*B65D 81/32*    (2006.01)
(Continued)

(52) U.S. Cl.
CPC .......... *B05C 17/00556* (2013.01); *A61C 5/64* (2017.02); *A61C 9/0026* (2013.01);
(Continued)

(58) Field of Classification Search
CPC ... A61C 5/64; A61C 9/0026; B05C 17/00509; B05C 17/00556; B65D 2251/04; B65D 81/325
See application file for complete search history.

(56) References Cited

U.S. PATENT DOCUMENTS 4,648,873 A    3/1987  Robinson
4,974,756 A   12/1990  Pearson et al.
(Continued)

FOREIGN PATENT DOCUMENTS

| EP | 0723807 A2 | 7/1996 | |
| EP | 2407249 A1 * | 1/2012 | ....... B05C 17/00506 |
| WO | 2007006030 A2 | 1/2007 | |

OTHER PUBLICATIONS

International Search Report and Written Opinion dated Sep. 24, 2015 in corresponding International Application No. PCT/EP2015/065466, filed Jul. 7, 2015.

*Primary Examiner* — David P Angwin
*Assistant Examiner* — Bob Zadeh
(74) *Attorney, Agent, or Firm* — Global IP Counselors, LLP

(57) ABSTRACT

A dispensing apparatus includes a body, two inlets for flowable masses and two outlets through which the flowable masses can be dispensed, with one inlet being connected to one outlet and the other inlet being connected to the other outlet through the body. The two inlets are spaced apart from one another by a first spacing and the two outlets are spaced apart from one another by a second spacing, and with the second spacing being larger than the first spacing. A connection ring engages the body and is pre-mounted to the body. The dispensing apparatus is configured to be non-releasably connected to a two-component cartridge via the connection ring for the supply of the flowable masses to the inlets.

22 Claims, 5 Drawing Sheets

(51) Int. Cl.
*A61C 9/00* (2006.01)
*A61C 5/64* (2017.01)

(52) U.S. Cl.
CPC .... *B05C 17/0052* (2013.01); *B05C 17/00509* (2013.01); *B05C 17/00553* (2013.01); *B65D 81/325* (2013.01); *B65D 2251/04* (2013.01)

(56) References Cited

U.S. PATENT DOCUMENTS

| | | | |
|---|---|---|---|
| 5,651,397 A * | 7/1997 | Black | A61C 9/0026 141/18 |
| 5,676,280 A | 10/1997 | Robinson | |
| 5,687,885 A | 11/1997 | Turk et al. | |
| 5,918,772 A | 7/1999 | Keller | |
| 6,286,722 B1 | 9/2001 | Fischer et al. | |
| 6,352,177 B1 * | 3/2002 | Bublewitz | A61C 9/0026 222/137 |
| 6,698,622 B2 | 3/2004 | Sawhney et al. | |
| 6,955,660 B2 | 10/2005 | Fisher | |
| 7,316,330 B2 * | 1/2008 | Muller | B05C 17/00506 222/145.6 |
| 7,468,049 B2 | 12/2008 | Laveault | |
| 7,694,853 B2 * | 4/2010 | Keller | B65D 81/325 215/332 |
| 7,815,384 B2 | 10/2010 | Parks et al. | |
| 7,988,684 B2 | 8/2011 | Cude | |
| 8,033,429 B2 * | 10/2011 | Keller | B05C 17/00506 222/137 |
| 8,052,421 B2 | 11/2011 | Pierson | |
| 8,074,843 B2 * | 12/2011 | Keller | B05C 17/00553 222/137 |
| 9,010,578 B2 * | 4/2015 | Keller | B01F 5/0615 222/137 |
| 9,138,772 B2 * | 9/2015 | Pappalardo | B05C 17/00553 |
| 9,168,108 B2 * | 10/2015 | Bublewitz | A61C 5/062 |
| 2001/0004082 A1 | 6/2001 | Keller | |
| 2005/0051576 A1 | 3/2005 | Brugner | |
| 2007/0235546 A1 * | 10/2007 | Strecker | B01F 7/246 235/492 |
| 2010/0163579 A1 | 7/2010 | Keller | |
| 2010/0318063 A1 | 12/2010 | Soll | |
| 2011/0045430 A1 * | 2/2011 | Kim | A61C 9/0026 433/36 |
| 2011/0056985 A1 * | 3/2011 | Bublewitz | B05C 17/00506 222/137 |
| 2011/0273956 A1 * | 11/2011 | Habibi-Naini | B05C 17/00503 366/190 |
| 2013/0023833 A1 * | 1/2013 | Kayser | A61M 5/19 604/232 |
| 2017/0182511 A1 * | 6/2017 | Hiemer | B05C 17/0052 |

* cited by examiner

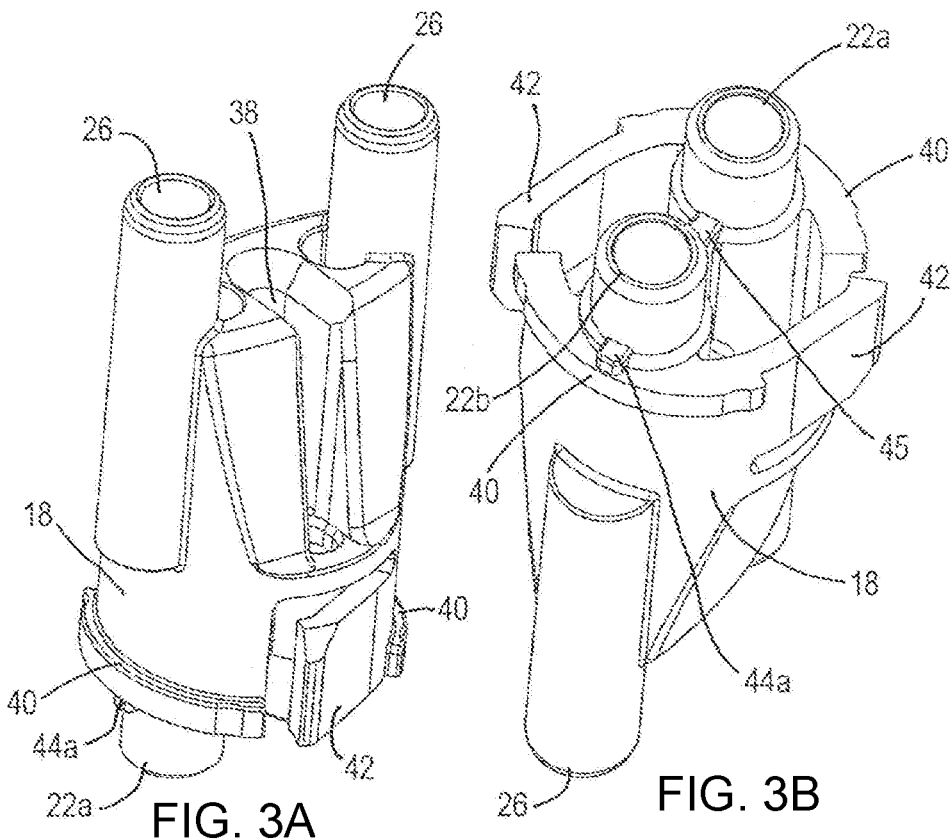
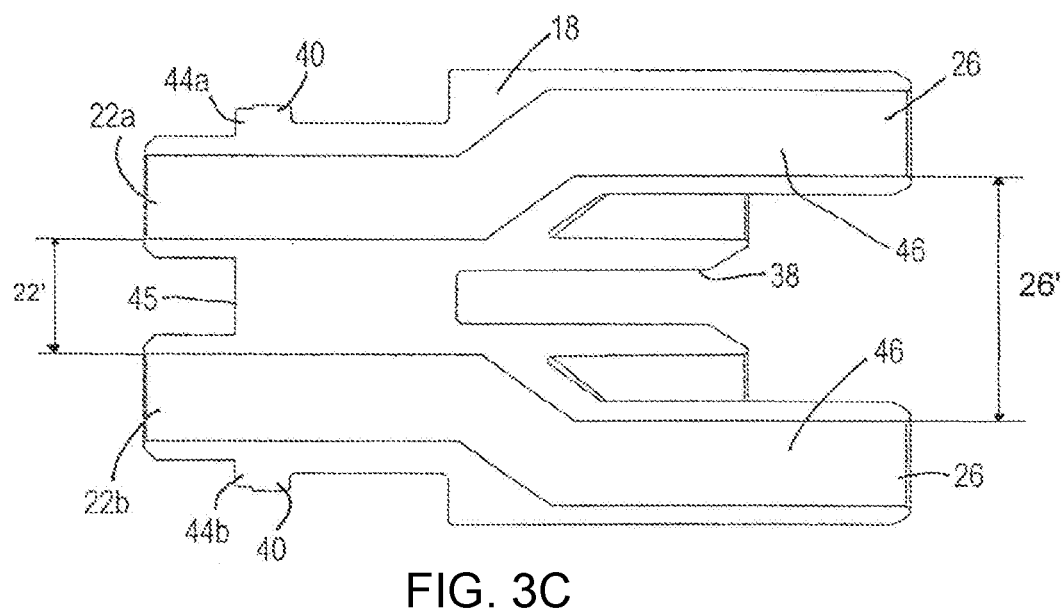
FIG. 3A
FIG. 3B
FIG. 3C

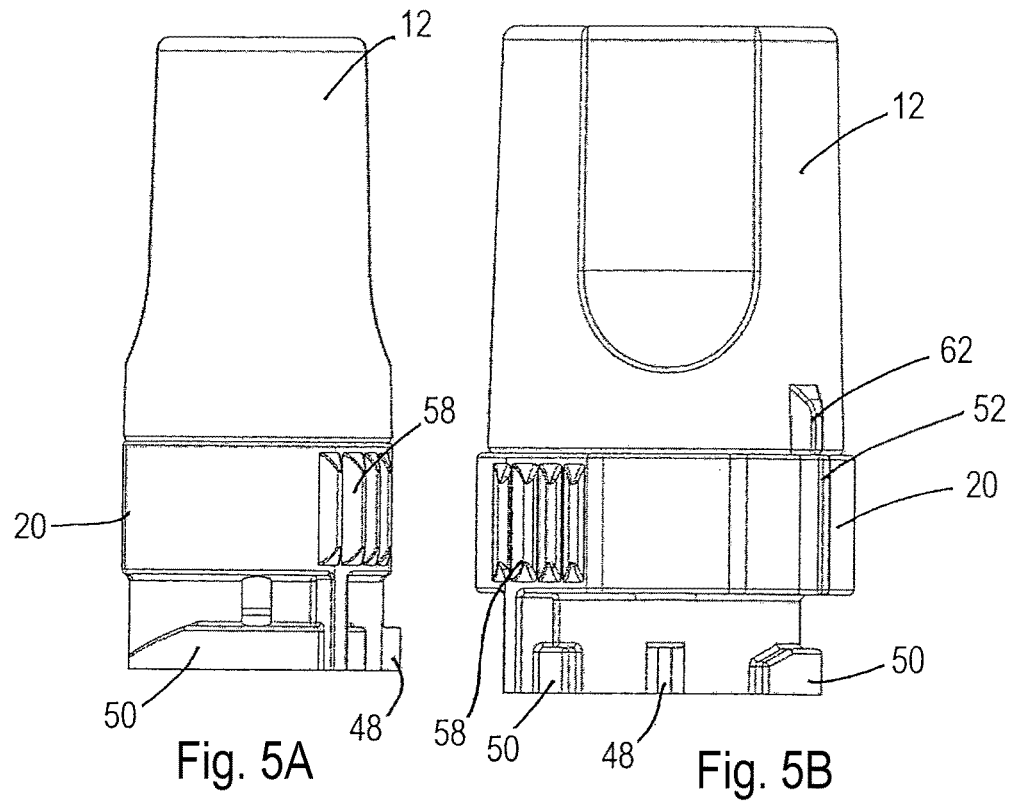
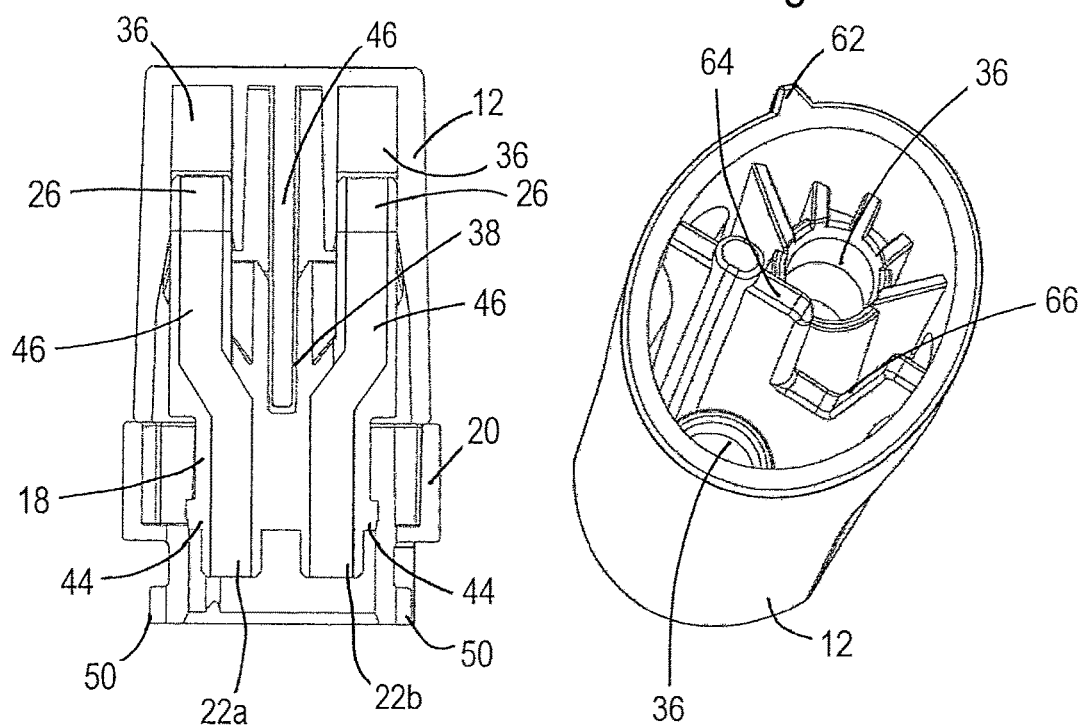

DISPENSING APPARATUS, DISPENSING SYSTEM AND METHOD OF DISPENSING

CROSS-REFERENCE TO RELATED APPLICATIONS

This application is a U.S. National Stage application of International Application No. PCT/EP2015/065466, filed Jul. 7, 2015, which claims priority to EP Application No. 14176325.0, filed Jul. 9, 2014 the contents of each of which is hereby incorporated herein by reference.

BACKGROUND

Field of Invention

The invention relates to a dispensing apparatus, to a dispensing system and to a method of dispensing flowable masses from a dispensing system.

Background Information

A wide variety of ways of dispensing two-component masses from cartridges is known in the prior art. The materials to be dispensed are typically a matrix material and a hardener. The filled cartridges come in different ratios referred to as 1:1, 2:1, 4:1 and 10:1 etc., the numbers specifying the ratios of the amounts of each of the two materials that are to be dispensed. The reason for these different ratios is to allow a wide variety of different compositions to be mixed and dispensed. For example, some compositions require more hardener and some require less hardener. Also some compositions require more mixing. Mixing tips are known from the prior art which are adapted to mix the compositions as they exit the cartridge. In this respect different length and different diameter mixing tips are provided to ensure a thorough through mixing of the two-components. The mixing tips typically have an insert resembling an open spiral which forces the two-components into contact with one another and exerts forces on them causing them to mix.

Two-component materials are typically used as impression materials, e.g. on the formation of dental impressions, as a cement material for prosthetic restorations, as a temporary cement for trial cementing restorations or for cementing temporary crowns. Further applications of two-component materials are in the building industry where they are e.g. used as a replacement for mechanical joints that corrode over time. Adhesive bonding can be used to bond products such as windows and concrete elements. The use of multi-component protective coatings, for example moisture barriers, corrosion protection and anti-slip coatings, is also becoming increasingly common. Examples of flowable materials which can be used are, for example, distributed by the company Coltene using the tradename AFFINIS® or by the company DMG using the tradename PermaCem.

SUMMARY

However, for some applications it can be desirable to not use such a mixing tip, but rather to use different ways of mixing the two-components in particular by hand. For this reason it is the object of the present invention to provide a dispensing apparatus which facilitates the dispensing, and therefore the mixing of two-components dispensed from a two-component cartridge.

This object is satisfied by a dispensing apparatus, comprising a body, two inlets for flowable masses and two outlets through which the flowable masses can be dispensed, with one inlet being connected to one outlet and the other inlet being connected to the other outlet through the body, wherein the two inlets are spaced apart from one another by a first spacing and the two outlets are spaced apart from one another by a second spacing, and with the second spacing being larger than the first spacing; and a connection ring which is adapted to engage the body and which is pre-mounted at the body; wherein the dispensing apparatus is adapted to be preferably non-releasably connected to a two-component cartridge via the connection ring for the supply of the flowable masses to the inlets.

In this connection it should be noted that pre-mounted means that the connection ring is attached to the body in some way. The connection ring is in particular attached to the body in such a way that it can be moved at least once relative to the body such that the connection ring can be moved from a storage position, in which the connection ring is stored at the body, to an engagement position, in which both the connection ring and the body engage a cartridge. In the engagement position the connection ring is preferably connected to the body in a non-releasable manner and the dispensing apparatus is likewise connected to the cartridge in a non-releasable manner in the engagement position.

Such a dispensing system is simple, therefore readily producible and hence cost-effective to realize. Such a dispensing system advantageously extends the outlet length of a two-component cartridge. The increased length of the outlets permits better control of the amount dispensed and its position of application, as the extended length lets the user see the point of application more clearly. Thus, such a dispensing apparatus can also be used in hand mixing applications.

Having regard to hand mixing applications, the dispensing system increases spacing present between the outlets. The added spacing leads to an avoidance of a cross-contamination, as the increased spacing with respect to the cartridge outlets ensures that the two-components cannot readily come into contact with one another.

It has to be noted that the body is to be understood as a part which acts as a guide for the two-components present in a cartridge. The guiding taking place between the outlets of the cartridge, the inlets of the dispensing apparatus and the outlets of the dispensing apparatus.

Advantageously the outlets of the dispensing apparatus have the same internal diameter as its inlets. It is also preferred if the passages connecting the respective inlets and the outlets have substantially the same diameter throughout the body of the dispensing apparatus. It can thereby be avoided that pressure variations arise on the dispensing of flowable masses via the dispensing apparatus. Such pressure variations can have negative effects on the mixing result, thus the avoidance of pressure variations leads to a uniform mixing of the two-components. Thus it can thereby be ensured that the full capabilities of e.g. a two-component adhesive can be obtained.

Advantageously the dispensing apparatus further comprises a closure cap adapted to cover the outlets. Such a closure cap beneficially enables the outlets to be closed off when the dispensing system is no longer in use. This increases the storage time of the materials stored in the two-component cartridge, as once opened, these typically have a shorter shelf life than for an unopened cartridge. Also the dispensing system can be stored without the flowable masses coming into contact with a storage environment.

Moreover, the closure cap can also prevent the two flowable masses, possibly present at the outlets, from coming into contact with one another and thereby avoids cross-contamination.

It is preferred if the closure cap is adapted to engage the body in one orientation only. This engagement preferably takes place without a rotation of the closure cap relative to the body. Thereby cross contamination of the outlets of the dispensing apparatus can successfully be avoided, since the closure cap cannot be placed onto the dispensing apparatus in different orientations between separate uses of the dispensing apparatus. This also increases the storage life of an opened cartridge.

Preferably the closure cap includes passages which substantially extend the outlets of the dispensing apparatus within the closure cap. This advantageously ensures that any flowable substance which may still be expelled via the outlets of the dispensing apparatus after a dispensing process has taken place can collect in the closure cap and does not result in an overpressure causing the closure cap to detach from the dispensing apparatus or a flow of substances back along an outside of the outlets of the dispensing apparatus. This means that the closure cap cannot become loose at a storage position of the dispensing apparatus and thereby enable a leak to take place there and possibly become a source of contamination at this position.

Advantageously the closure cap further comprises a flexible portion which is adapted to engage the body and thereby ensures a connection between the closure cap and the dispensing apparatus.

By such a flexible portion, e.g. in the form of a flexible nose, the closure cap is able to engage the dispensing apparatus and the closure cap falling off from the dispensing apparatus can thereby be avoided. In another example, the flexible portion can be part of a snap-on connector assembly which engages a respective groove or recess then present at the dispensing system, with the flexible portion permitting a removal of the closure cap.

It is particularly preferred that the closure cap and the dispensing apparatus comprise a coded alignment means (or device) for a coded alignment of the cap and the dispensing apparatus. Thereby, a false placement of the closure cap onto the dispensing apparatus can be avoided.

In this connection it should be noted that in the framework of this invention a coded alignment relates to a rotational alignment of the components in question, i.e. that these can only be connected in certain rotational orientations, may be only in one.

The coded alignment device can be present internally and/or externally at the closure cap and/or at the dispensing apparatus. An external alignment means (or device) can be components which have an optical alignment function, i.e. the components of such optical alignment means (or device) do not cooperate with one another in a physical sense, but enable a visual alignment of the closure cap and the dispensing apparatus to take place.

In contrast to this, an internal alignment means (or device), and in this regard thus non-optical alignment means (or device) have the function of physically cooperating with one another, so that the closure cap can be aligned with the dispensing apparatus for a correct placement of the closure cap at the dispensing apparatus in a few positions only. In this connection it must be noted that the external alignment device can also be designed such they physically cooperate with one another in addition to providing an optical alignment function.

In this way it is preferred if the coded alignment device is formed by at least one nose and by at least one corresponding groove. The nose and the groove being configured to cooperate with one another, this means that the nose can e.g. be introduced into the groove. In dependence on the selected position of the nose and the groove at the closure cap and the dispensing apparatus one can ensure that if the closure cap is placed onto the dispensing apparatus in an unwanted orientation, then the nose cannot engage that groove, so that the closure cap can only engage the dispensing apparatus in one orientation.

In such a situation, the groove is e.g. arranged off-center at the body, so that if the closure cap is placed onto the dispensing apparatus rotated by e.g. 180° to the desired orientation then the nose would not engage the groove, but rather e.g. a blocking element, thereby the position of the nose and the groove is selected such the closure cap can only be placed onto the dispensing system in one orientation.

It is thereby ensured that the user cannot place the closure cap fully onto the dispensing apparatus. The nose can be present at either the closure cap or at the dispensing apparatus and the groove can then respectively be present at either the dispensing apparatus or at the closure cap, wherein the nose is adapted to be inserted into the groove. It is preferred if the groove is present at the body.

The coded alignment device can be disposed in a symmetric or an asymmetric manner at either of the closure cap and the dispensing apparatus. A symmetric coded alignment means (or device) can be an alignment means (or device) having the same size, but which are arranged such that the closure cap and the dispensing apparatus can only be connected in certain orientations, whereas the asymmetric coded alignment device can have varying sizes.

Also a plurality of noses can be present at the closure cap and cooperate with a corresponding plurality of grooves present at the dispensing apparatus. These are examples of different types of coded alignment devices which can beneficially help avoid a cross-contamination of components stemming from the respective outlets, as they permit the respective parts from being connected wrongly.

In a preferred embodiment, a length of the outlets of the dispensing apparatus is longer than a length of the outlets of the cartridge; and/or wherein the dispensing apparatus extends a length of the outlets of the cartridge when mounted at a cartridge.

By extending the length of the outlets, simpler dispensing of the components from the cartridge becomes possible, as a larger angular spread of angles of application become possible. This is because the longer the length of the outlets, the better the handling of the cartridge becomes and thus a more accurate dispensing of the components can be achieved.

Advantageously the connection between the dispensing apparatus and the two-component cartridge is brought about by a latching and/or a rotation of the dispensing apparatus to the two-component cartridge. Such attachment mechanisms are simple to realize, i.e. are cost effective, and bring about a secure connection between the components and thus facilitate the handling of the dispensing apparatus.

In a preferred design the connection between the dispensing apparatus and the two-component cartridge is a non-releasable connection. Providing a non-releasable connection helps to avoid possible cross-contamination of the dispensing apparatus when this is used at different cartridges where a hardener may not always be present in the first chamber of a further cartridge, but rather can also be present in a second chamber of the further cartridge.

In a preferred embodiment of the dispensing apparatus, this further comprises a connection ring which is adapted to engage the body and the two-component cartridge, wherein the engagement at the body is brought about at a shoulder of the body. Such a connection ring can facilitate the connection of the body to the cartridge, via the shoulder, in order to ensure that the body is correctly aligned at the cartridge and to ensure that the body is securely held in place via the shoulder and to also prevent a removal of the body from the cartridge. If the body is not securely held at the cartridge the outlets of the cartridge and the inlets of the dispensing apparatus may not be correctly aligned and therefore material could escape between the outlets and the inlets, which is clearly unfavorable. Such two part dispensing apparatuses are universally applicable and can be produced in a cost effective manner.

Advantageously the pre-mounting of the connection ring at the body is brought about by frictional engagement between the connection ring and the body. The frictional engagement permits the connection ring to be held at the body in a storage state of the dispensing apparatus and thereby ensures a correct placement of the dispensing apparatus at a cartridge. This is because the connection ring permits correct alignment of the dispensing apparatus and a cartridge.

At least one portion is preferably disposed at the connection ring that is adapted to bring about the frictional engagement between the body and the connection ring to establish the pre-mounting. This frictional engagement, in particular, takes place between the outlets of the body and the connection ring. The portion effectively exerts a pressure on the body and thereby holds the body relative to the connection ring. Such a portion is simple to manufacture and can take the shape of e.g. a projection or an elevation.

This at least one portion can in particular act as a prevention means (or device) in order to prevent the inlets of the body from being axially moved in the direction opposite to an insertion direction. This is because the at least one portion can act as an abutment that prevents the movement of the connection ring in this direction.

Advantageously the pre-mounted connection ring is non-releasably connected to the body following a rotation of the connection ring relative to the body, i.e. in a dispensing position of the dispensing apparatus.

The non-releasable connection between the pre-mounted connection ring and the body can in particular be activated by an axial displacement of the connection ring in a direction away from the outlets and by a rotation of the connection ring relative to the body.

Advantageously the connection ring is adapted to engage the two-component cartridge after a rotation relative to the body and the inlets. Providing a rotatable connection ring enables this to be attached to the cartridge using e.g. bayonet connection means (or devices) or threaded connection portions. Moreover, it enables the body to be correctly aligned with respect to the cartridge prior to locking this in place by a rotation of the connection ring.

Advantageously the connection between the connection ring and the two-component cartridge is adapted to be brought about by respective bayonet attachment devices connecting the connection ring and the body to the two-component cartridge. These enable a quick connection, are simple to manufacture and also facilitate a coded alignment if the bayonet connection devices are e.g. asymmetrically arranged at the connection ring or have different sizes.

In a preferred embodiment of the dispensing apparatus, the body further comprises a locking means (or device) to lock the connection ring to the body once the connection between the connection ring and the two-component cartridge has been established to form a non-releasable connection, with the locking preferably taking place automatically, and with the locking device preferably being formed by elastic arms which engage into respective cutouts provided at the connection ring.

The locking device reliably ensures e.g. that the connection ring cannot be rotated relative to the body when it has been locked into place, such a locking being brought about by the elastic arms. Thus, the locking device ensures blocking of the rotational movement of the connection ring and can thus be considered as a rotational lock.

The locking device could alternatively or additionally also ensure an axial locking of the body relative to the connection ring.

The locking device is advantageously provided to lock the dispensing apparatus to the cartridge. If the connection ring is locked into a position with respect to the body, i.e. the connection ring cannot be moved relative to the body, then the dispensing apparatus cannot be removed from the cartridge in this locked position e.g. if the dispensing apparatus is attached to the cartridge by means of a rotational movement of the connection ring. This then ensures that a non-releasable connection of the dispensing apparatus to the cartridge is affected. This also ensures that no cross-contamination can take place near the outlets of the cartridge. The locking device can be provided both at the body and at the connection ring.

By elastic arms, the body can be fixed relative to the connection ring once this has completely engaged the cartridge. If the connection has a ramp like portion which the elastic arms engage during the rotation followed by a sharp jump which the elastic arms follow, these can easily be locked into position. Naturally speaking, the elastic arms could also be provided at the connection ring and engage a corresponding cut out provided at the body.

In a further preferred embodiment of the dispensing apparatus, this further comprises a device for a coded alignment of the dispensing apparatus relative to the two-component cartridge, the means preferably being formed by at least one nose and at least one corresponding groove which are configured to cooperate with one another and which are preferably provided at the bayonet device and/or by an unsymmetrical bayonet device.

The coded alignment device ensures that the dispensing apparatus can only be installed at the cartridge in one rotational orientation. This advantageously avoids a cross-contamination of the outlets of the cartridge being brought about. Cartridges are typically supplied having a universal coded alignment means (or device). Providing a dispensing apparatus with the counter partners means that this can be universally used.

In a further aspect of the present invention this relates to a dispensing system comprising a dispensing apparatus as discussed herein and a two-component cartridge, the two-component cartridge optionally being filled with two flowable masses.

In such a dispensing system the dispensing apparatus can be configured in such a way that the inlets of the dispensing system are very well matched to the outlets of the dispensing system. Moreover, the connection between the dispensing apparatus and the cartridge can be ideally matched to ensure a tight connection. Thereby it can be ensured that the two-component masses discharged from the cartridge do not leak into the dispensing apparatus. Such a leak could cause a cross contamination. A cross contamination has to be avoided as it would cause the two-components to prematurely react and to block at least one of the inlets of the dispensing system or the outlets of the cartridge rendering these unusable.

Such a dispensing system can be distributed to manufacturers of the two-component masses and can then be filled with two-component material to be dispensed.

Typical dispensing systems have volumes for the flowable masses selected from the range of volumes comprising 2.5 ml, 5 ml, 10 ml, 20 ml, 50 ml and 100 ml, with the volume being a combined volume for both chambers of the cartridge. Thus, in a preferred embodiment the dispensing system has a volume in the range of 1 to 100 ml.

In a further aspect of the present invention this relates to a method of dispensing flowable masses from a dispensing system as discussed herein, wherein the method comprises the steps of first dispensing the flowable masses from the dispensing system and optionally carrying out a subsequent mixing of the flowable masses by hand.

This means that the flowable masses are discharged from the cartridges via the dispensing apparatus by hand so that a subsequent mixing can take place either by hand or using a mixing apparatus which is different from a mixing tip.

In this regard mixing by hand means that the flowable masses discharged from the cartridges are mixed e.g. using a spatula to mix the masses in a container or on a flat surface etc.

BRIEF DESCRIPTION OF THE DRAWINGS

Referring now to the attached drawings which form a part of this original disclosure.

FIGS. 3A-3C are views of a body (FIGS. 3A and 3B) and a section through the body (FIG. 3C);

FIGS. 5A-5D are views of a dispensing apparatus (FIGS. 5A & 5B), a section through the dispensing apparatus of FIG. 5B (FIG. 5C) and a view of the closure cap (FIG. 5D)

DETAILED DESCRIPTION OF THE EMBODIMENTS

Figures 1, 2:
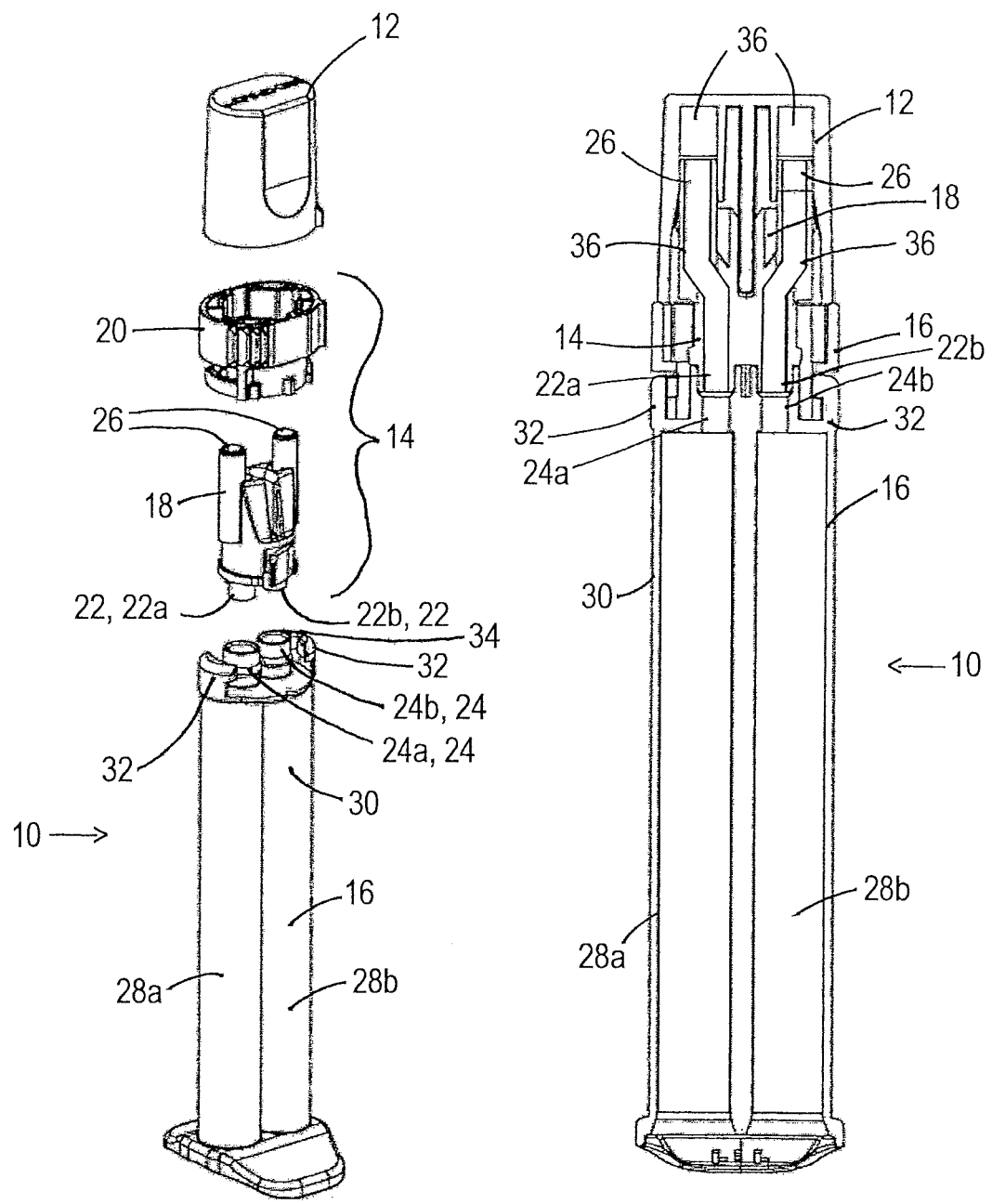
FIG. 1 is an exploded view of the components of a dispensing system.
FIG. 2 is a section through the assembled dispensing system of FIG. 1.

Features which have the same or a similar function will be described in the following using the same reference numeral. It is also understood that the description given with respect to reference numerals used in one embodiment also applies to the same reference numerals in connection with other embodiments unless something is stated to the contrary.

FIG. 1 shows an exploded view of the components of a dispensing system 10. The dispensing system 10 comprises a closure cap 12, a dispensing apparatus 14 and a two-component cartridge 16. As can be seen, the dispensing apparatus 14 comprises a body 18 as well as a connection ring 20. The body 18 has two inlets 22a, 22b for flowable masses which are connectable to outlets 24a, 24b of the two-component cartridge 16. The body also has two outlets 26 through which the flowable masses can be dispensed. The one inlet 22a can be connected to the one outlet 24a of the two-component cartridge 16 and the other inlet 22b can be connected to the other output 24b of the two-component cartridge 16. Thus, the dispensing apparatus 14 is adapted to be connected to a two-component cartridge 16 for the supply of the flowable masses to the inlets 22a, 22b of the dispensing apparatus 14.

In a storage state and/or in a transport state the closure cap 12 simply fits on the outlets 26 of the dispensing apparatus 14 and thus seals the outputs 26 of the dispensing apparatus 14 from the outside.

The two-component cartridge 16 shown in FIG. 1 has two chambers 28a, 28b to store two respective components of e.g. a two-component adhesive. At the end 30 of the cartridge 16, where the outlets 24a, 24b from the cartridge 16 can be seen the cartridge 16 is equipped with attachment means, such as bayonet prongs 32 which are adapted to cooperate with corresponding bayonet lugs 50 (see FIG. 4) of the dispensing apparatus 14. Moreover, the two-component cartridge can comprise a cutout 34 which can interact with a corresponding nose 48 (see FIG. 4A) as a coded alignment means.

The two-component cartridge 16 shown here can be configured like the component cartridge disclosed in EP 0 730 913, whose contents is hereby included by reference. Corresponding markings can be provided at the dispensing apparatus 14 in order to ensure that this is correctly installed at the cartridge (see the bottom view of FIG. 4A). This in particular ensures that a cross-contamination between the cartridge 16 and the dispensing apparatus 14 cannot occur if the dispensing apparatus 14 is used for multiple applications.

The cartridge 16 illustrated in FIG. 1 is a so-called 1:1 cartridge 16, but can easily be replaced by 2:1, 4:1 and 10:1 cartridges in dependence on the desired use of the materials stored in the cartridge and the desired application.

FIG. 2 shows a section through the assembled dispensing system 10 of FIG. 1. As can clearly be seen there is a direct connection between passages 36 of the closure cap 12 which are adapted to receive the outlets 26 of the body 18 and the outlets 24a, 24b of the cartridge 16 when the dispensing system 10 is assembled. This direct connection permits the dispensing of the flowable masses possibly present in a cartridge 16 from the cartridge 16 through the dispensing apparatus 14 out of the outlets 26 of the dispensing system 10 on an application of a plunger (not shown). The plunger is generally used to dispense the flowable masses from the two-component cartridge 16.

FIG. 3A shows a view of the body 18 of a dispensing apparatus 14. The body 18 has two outlets 26, two inlets 22a, 22b (of which only one 22a is shown in this example). At the center of the body 18, a groove 38 can be seen which is adapted to cooperate with a corresponding nose of a closure cap 12 (see FIG. 5D with respect to the closure cap 12). The inlets 22a, 22b of the body 18 are spaced apart from one another by a first spacing and the two outlets 26 are spaced apart from one another by a second spacing, with the second spacing being larger than the first spacing. The body 18 is adapted at its end comprising the inlets 22a, 22b to be connected to a two-component cartridge 16 for the supply of flowable masses.

Figure 4A:
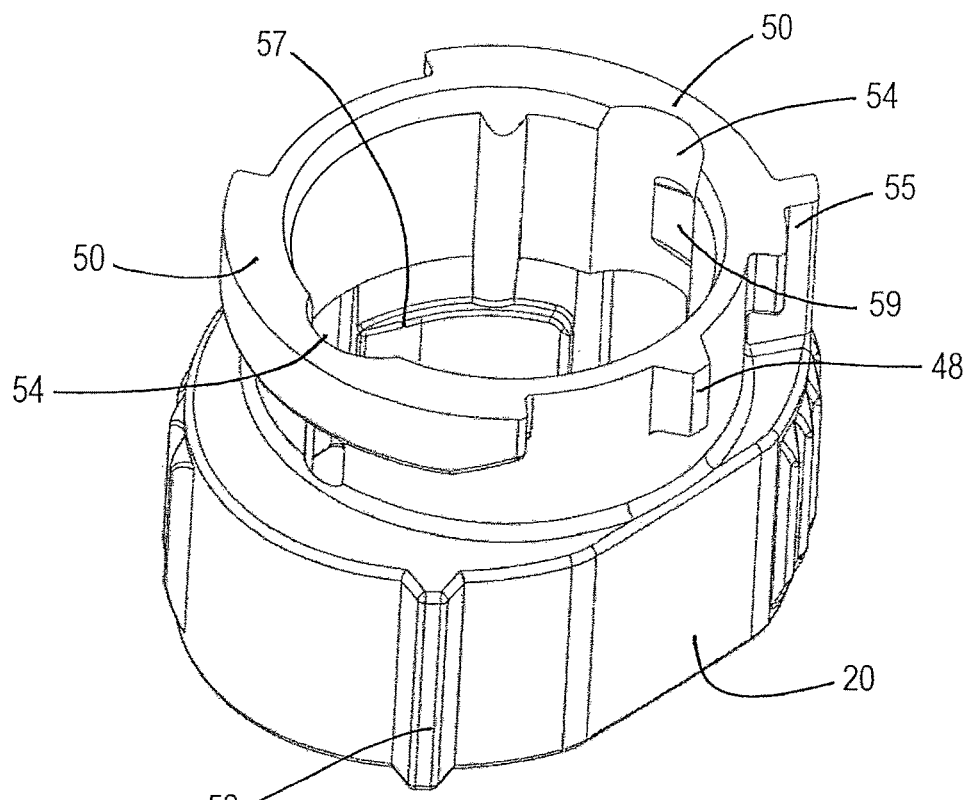
FIGS. 4A-4B are views of a connection ring.
Figure 4B:
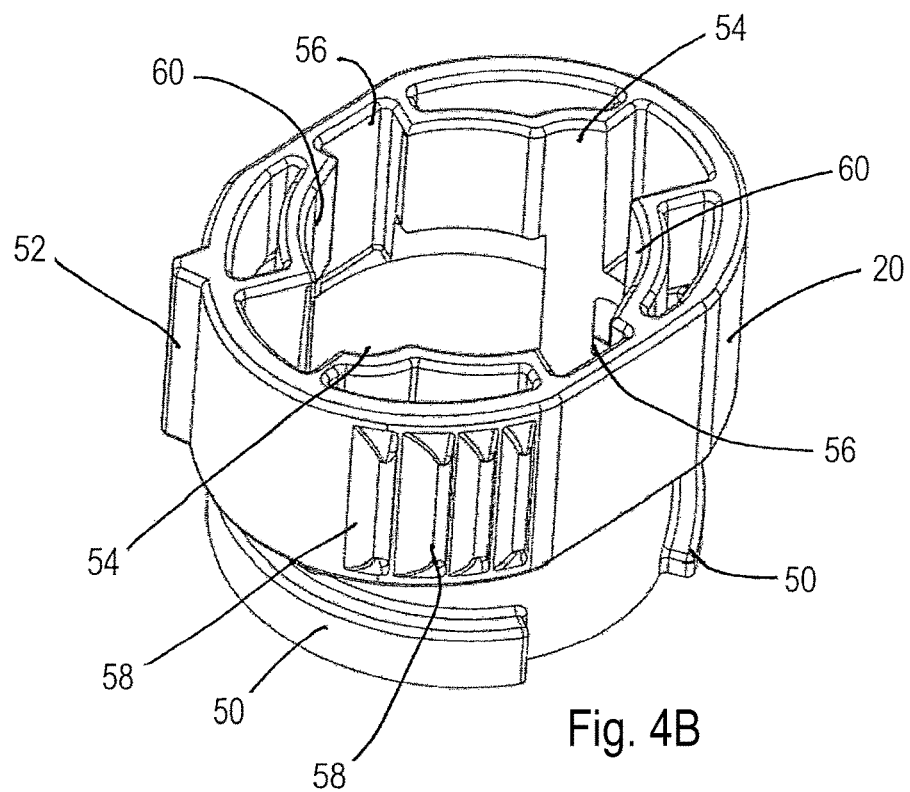

FIG. 3B shows a bottom view of the body 18, shoulders 40 can be seen which cooperate with the connection ring 16 (see FIG. 4B for the corresponding counter parts). As can also be seen at the lower end of the body 18 there are elastic arms 42 which extend outwardly and which are adapted to engage corresponding cutouts 54 of the connection ring 20 (see FIG. 4B). This engagement taking place once the apparatus has been placed on the cartridge 16 and the connection ring 20 has been rotated into the final position.

These elastic arms 42 are provided such that the dispensing apparatus 14 cannot be removed from the cartridge 16. This means that bodies having such elastic arms 42 are generally only used with one cartridge 16. Nevertheless, these elastic arms 42 do not have to be provided, so that the dispensing apparatus 14 can be used a multiple of times with a variety of different cartridges 16.

Also shown are noses 44a (see FIGS. 3A to 3C), and 44b (see FIG. 3C), as well as a web 45 (see FIGS. 3B and 3C) which act as an axial abutment of the body 18 relative to the cartridge 16 when the body 18 is placed onto the cartridge, this means that the noses 44a, 44b and the web 45 define a maximum insertion length which the inlets 22a, 22b of the body 18 can be inserted into the outlets 24a, 24b of an associated cartridge 16.

FIG. 3C shows a section through the body 18 of FIG. 3A. The groove 38 of the body 18 forms an internal coded alignment means for indicating how the closure cap 12 can be installed at the dispensing apparatus 14. Moreover, two passages 46 present within the body 18 which connect the inlets 22a, 22b of the body 18 to the outlets of the body 18 can be seen. In this example, the passages 46 are of essentially Z-shape. Curved passages or passages of a different kind of shape could also be provided, as long as the shape of the passages 46 ensures that the inlets 22a, 22b are spaced apart from one another by a first spacing and the two outlets 26 are spaced apart from one another by a second spacing with the second spacing being larger than the first spacing. FIG. 3C further shows a first spacing 22' present between the first and second inlets 22a, 22b of the body 18 and a second spacing 26' present between the outlets 26 of the body 18. The second spacing 26' is larger than the first spacing 22'.

FIGS. 3A and 3B show that the two outlets 26 and the two inlets 22a, 22b (of which only one 22a is shown in this example) have a generally tubular form and have a generally circular outlet opening respectively a circular inlet opening. The tubular parts forming the outlets 26 of the dispensing apparatus 14 project beyond the body 18 of the dispensing apparatus 14 to facilitate a dispensing therefrom.

In an exemplary embodiment it is preferred if the tubular outlets 26 project beyond the body 18 (see e.g. FIG. 3C in this regard), by up to 20 to 30% of the length of the body 18.

In accordance with FIG. 3C one can see that a diameter of the flow path between the inlets 22a, 22b and the outlets 26 of the dispensing apparatus 14 is at least substantially the same over the length of the outlet path. In particular, the diameter of the flow path is the same between the inlet opening and the outlet opening over the length of the outlet path.

Moreover, in the embodiment shown in FIG. 3C both the inlets 22a, 22b and the outlets 26 project from the body 18, wherein the inlets 22a, 22b project less far from the body than the outlets 26 of the dispensing apparatus 14.

In this connection it must be noted that the outlets 26 have a certain length and diameter and in the present example have a tubular shape with a circular outlet opening at one end thereof. Moreover, the inlets 22a, 22b also have a certain length and diameter and in the present example have a tubular shape with a circular inlet opening at one end thereof.

Both the inlets 22a, 22b and the outlets 26 are present at the body 18 of the dispensing apparatus 14. The outlets 26 are present at the body 18 at two opposite sides of the body 18, whereas the inlets 22a, 22b are present at the body 18 at an end face thereof.

Moreover, the openings of the outlets 26 open at least substantially in parallel to the longitudinal axis of the body 18, this means that a substance present in a cartridge 16 attached to the dispensing apparatus 14 can be dispensed in the same direction as the pistons (not shown) of the cartridge 16 are moved to dispense a substance present therein.

FIGS. 4A and 4B show bottom and top views of the connection ring 20 of the dispensing apparatus 14. The bottom view of FIG. 4A shows the bayonet connection device which comprises two bayonet lugs 50 which are adapted to cooperate with corresponding bayonet connection device 32 provided at the cartridge 16.

Also shown is a projection 52, which acts as an external coded alignment device for a coded alignment of the closure cap 12 with respect to the dispensing apparatus 14. Further cutouts 54 are seen in the connection ring 20 which facilitate the axial movement of the connection ring 20 relative to the body 18 on an installation of the connection ring 20 at the body 18 to form a dispensing apparatus 14. In particular, two cutouts 54 can be seen through which the outlets 26 of the body 18 can be guided. Also visible is a projection 55 (in this regard see also FIGS. 6C and 6D). A ridge 57 is also seen which cooperates with the shoulder 40 of the body 18 in order to axially secure the body at the cartridge 14.

A portion 59 can be seen in FIG. 4A, this portion is adapted to frictionally engage the outlets 26 of the body 18 on the assembly of the connection ring 20 and the body 18 to the dispensing apparatus 14. Once the outlets 26 have passed the portion 59, the portion 59 can act as a prevention device in order to prevent the inlets 26 of the body 18 from axially moving in the direction opposite to the insertion direction. This means that the portion 59 can act like a shoulder which the outlets 26 then cannot overcome once assembled to a dispensing apparatus 14.

Moreover, during storage of a dispensing apparatus 14 prior to the attachment to the cartridge 16, the outlets 26 can be positioned such that they are in engagement with the portion 59 and are thereby axially held in a position such that they cannot become disengaged from the one another. Therefore, the portion 59 prevents the body 18 from becoming detached from the connection ring 20. The second cutout 54 of the connection ring 20 can naturally also comprise such a portion (not shown).

Figures 6A, 6B:
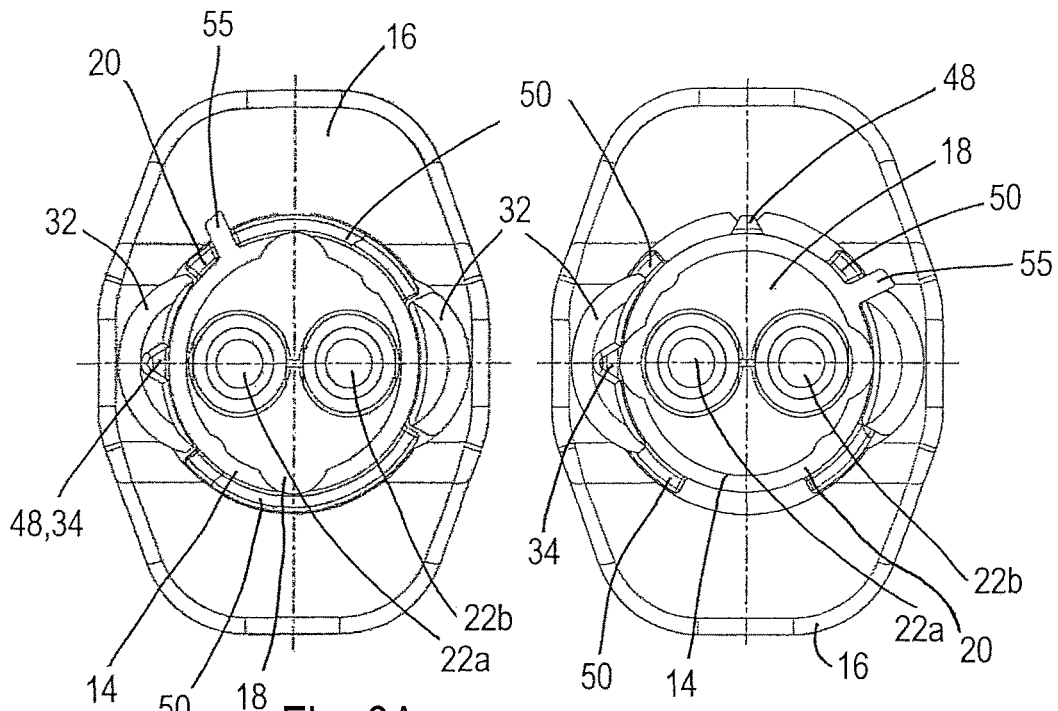
FIGS. 6A-6D are sections of the dispensing system from above in different positions of use.
Figures 6C, 6D:
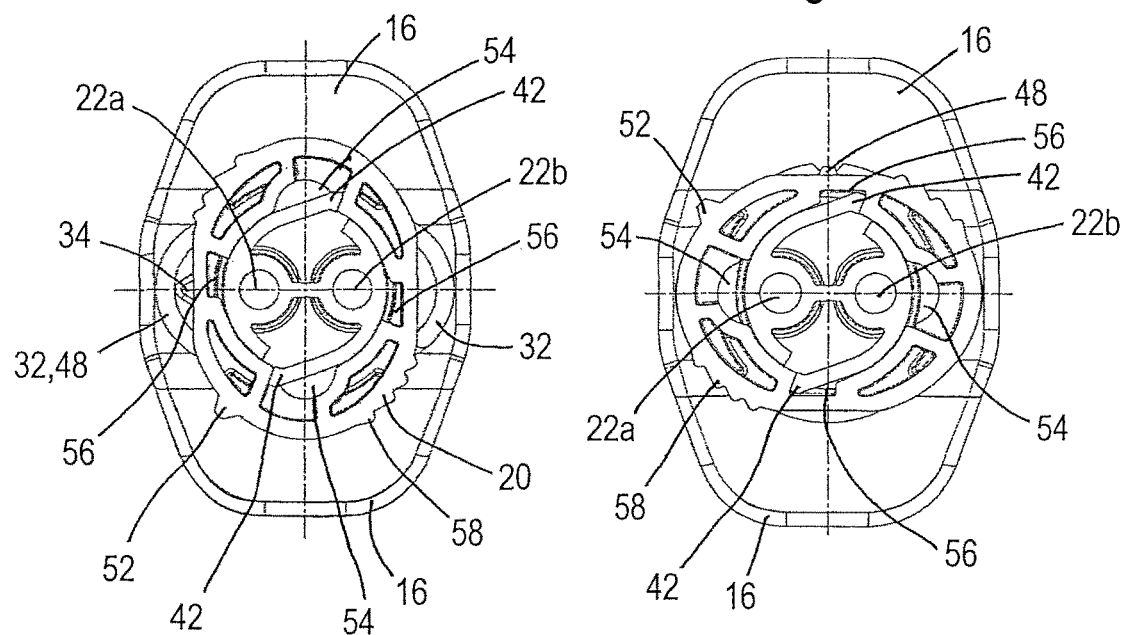

FIG. 4B shows smaller recesses 56 which are configured to permit the elastic arms 42 of the body 18 to be locked into position in the connection ring 20 on the assembly of a dispensing apparatus 14 (see also FIG. 6D). The connection ring 20 further includes ribs 58, which are used to increase the grip a user has on a rotation of the connection ring 20 to ensure a secure locking of the dispensing apparatus 14 to the cartridge 16.

FIG. 4B shows a top view onto the connection ring of FIG. 4A. The cutouts 54 for the outlets of the body 18 can also be seen, as can the retention device 56 used to cooperate with the elastic arms 42 in order to lock the connection ring 20 into a fixed rotary arrangement when the dispensing apparatus 14 has been installed at a cartridge 16 to form a dispensing system 10.

The connection ring 20 is locked to the body when the body 18 has been placed such that the inlets 22a, 22b of the body 18 are aligned with the outlets 24a, 24b of the cartridge 16 by simply rotating the connection ring 20 by 90° with respect to the cartridge 16 and the body 18. This locking is due to the elastic arms 42 which can move in the cutouts 54 and can ride along the smooth internal surface 60 of the connection ring 20 and then jump into the retention space 56 in the form of a recess, once the connection ring 20 has been rotated by 90°. The recess 56 act as ramps which the elastic arms 42 cannot overcome when an attempt is made to rotate the connection ring 20 into the opposite direction or further in the same direction. Thus, the elastic arms bring about a rotational fixation of the connection ring 20 with respect to the body 18.

Due to the rotational fixation of the connection ring 20 relative to the body 18, the bayonet connection device 32, 50 cannot be disengaged also bringing about an axial fixation of the dispensing apparatus relative to the cartridge. Hence the dispensing apparatus 14 cannot be removed from the cartridge 16 without excessive force. This force preferably being so large that the connection ring 20 is at least considerably impaired if not destroyed once applied.

FIGS. 5A to 5D show different views of the closure cap 12. In FIG. 5A the view of the closure cap 12 from one side can be seen in its installed position at the dispensing apparatus 14, whereas FIG. 5B shows a further view of the dispensing apparatus 14. The side view of FIG. 5B has a projection 62 which is provided to align with the projection 52 of the dispensing apparatus 14 in order to provide a visual coded alignment device or system so that the closure cap 12 can always be placed onto the dispensing apparatus 14 by means of a visual alignment.

FIG. 5C shows a section through the closure cap 12 and the dispensing apparatus 14. As can be seen, the closure cap 12 has a nose 64 which engages the groove 38 of the body 18. The nose 64 and the groove 38 are an internal coded alignment device or system. Moreover, the closure cap 12 has two passages 36 which receive the outlets 26 of the dispensing apparatus 14. These passages 36 are designed in such a way that after the use of the dispensing apparatus 14 the flowable masses still present at the outlets 26 can flow into these passages 36 without a backward flow being provided. This backward flow could be present if no such space is provided. The backward flow would lead the flowable masses back on the outside of the outlets 26 towards the groove 38 of the body 18 where one of the two-component materials could possibly come into contact with a second component of the two-component adhesive and cure there effectively locking the closure cap 12 to the dispensing apparatus 14 and at least providing a source of cross-contamination. At worst a complete cartridge 16 including an expensive adhesive is rendered unusable by such a cross contamination.

FIG. 5D shows a bottom view of the closure cap 12. On the one hand, the external visual coded alignment device in the form of the projection 62 and, on the other hand the internal coded alignment device in the form of a flexible portion or nose 64 and a further cutout 66 can be seen. The internal coded alignment device is dimensioned in such a way that the closure cap 12 always only cooperates with the dispensing apparatus 14 in one position. Therefore, the coded alignment device ensures that the closure cap 12 can only be installed at the dispensing apparatus 14 in one orientation.

FIG. 6A shows a top view onto a dispensing system 10 without a closure cap 12 being installed at the dispensing system 10. As can be seen, the cartridge 16 has the bayonet attachment device 32 which cooperates with the bayonet attachment device 50 of the connection ring 20. One of the bayonet prongs 32 has a cutout 34 for the alignment of the nose 48 in order to provide a further coded alignment means during the attachment of the dispensing apparatus 14 to the cartridge 16.

FIG. 6A shows a section through the dispensing apparatus when it is installed at the cartridge, but the connection ring 20 has not been rotated to fixedly connect the dispensing apparatus 14 to the cartridge 16. The section is taken at a position just above the bayonet attachment means 32, 34 of the cartridge 16. One can clearly see the bayonet attachment device 32 at the cartridge, these are provided in the form of bayonet prongs 32 and a cutout 34 which cooperate with the nose 48 and the bayonet lugs 50 provided at the connection ring 20 (see e.g. FIG. 4A)

In contrast to this, FIG. 6B shows a section through the dispensing apparatus 14 at the same height when the connection ring 20 has been rotated by 90°. This rotation by 90° can be seen from a comparison of the different positions of the external protrusion 55 present at the connection ring 20.

FIGS. 6C and 6D show further sections through the same arrangement as shown in FIGS. 6A and 6B, the difference being that the section is taken at the height of the elastic arms 42. In FIG. 6C the elastic arms 42 are present in the cutout 54 and can be moved freely there and along the smooth internal surface 60. Once rotated as shown in FIG. 6D the elastic arms 42 are in engagement with the recess 56, and indeed in such a way that the connection ring 20 is locked into a position in which it cannot be rotated back into the starting position relative to the body 18 due to the elastic arms 42 engaging the respective retention means 56.

The dispensing system 10 is typically manufactured from a plastic in an injection molded process. As illustrated in the Figures above, the dispensing apparatus 14 comprises at least two parts. The dispensing system 10 can naturally be filled with a two-component adhesive such as is typically used at building sites and/or in the dental field or in other fields where two-component masses are used. The dispensing system 10 is preferably used for hand-mixing applications. This means that the masses are dispensed from the chambers 28a, 28b of the cartridge 16 via the dispensing apparatus 14 to a point of application where these masses are either mixed by hand or are applied into a mixing apparatus (not shown) for their mixing.

Although the invention has been described with regard to a two-component system, a dispensing apparatus having three or more inlets and corresponding three or more outlets for a three- or multi-component system can naturally also be employed using the concept of the present invention, as long as a spacing between the respective outlets is larger than a spacing between the inlets.

The invention claimed is:
1. A dispensing apparatus, comprising:
a body, first and second inlets for flowable masses and first and second outlets through which the flowable masses are capable of being dispensed, with the first inlet being connected to the first outlet and the second inlet being connected to the second outlet through the body, the first and second inlets being spaced apart from one another by a first spacing and the first and second outlets being spaced apart from one another by a second spacing, the second spacing being larger than the first spacing, the body defining a first outer surface at the first outlet and a second outer surface at the second outlet, the first and second outer surfaces at least partially facing each other and being spaced from each other so as to form a gap therebetween; and
a connection ring configured to engage the body and being pre-mounted at the body,
the dispensing apparatus being configured to be non-releasably connected to a two-component cartridge via the connection ring for supply of the flowable masses to the first and second inlets.

2. The dispensing apparatus in accordance with claim 1, further comprising a closure cap configured to cover the first and second outlets.

3. The dispensing apparatus in accordance with claim 2, wherein the closure cap is configured to engage the body in one orientation only.

4. The dispensing apparatus in accordance with claim 2, wherein the closure cap comprises a flexible portion configured to engage the dispensing apparatus and to thereby ensure a connection between the closure cap and the dispensing apparatus.

5. The dispensing apparatus in accordance with claim 2, wherein the closure cap and the dispensing apparatus comprise coded alignment system configured to enable coded alignment of the closure cap and the dispensing apparatus.

6. The dispensing apparatus in accordance with claim 5, wherein the coded alignment system is formed by at least one nose and at least one corresponding groove which are configured to cooperate with one another, the at least one nose is disposed at one of the closure cap and the dispensing apparatus and the groove is disposed at the other of the dispensing apparatus and the closure cap, and the at least one nose is configured to be inserted into the at least one groove.

7. The dispensing apparatus in accordance with claim 2, wherein the closure cap includes passages which extend the first and second outlets of the dispensing apparatus within the closure cap.

8. The dispensing apparatus in accordance with claim 1, wherein a length of the first and second outlets of the dispensing apparatus is longer than a length of the outlets of the cartridge.

9. The dispensing apparatus in accordance with claim 1, wherein the pre-mounting of the connection ring at the body is caused by a frictional engagement between the connection ring and the body.

10. The dispensing apparatus in accordance with claim 9, further comprising a system for coded alignment of the dispensing apparatus relative to the two-component cartridge.

11. The dispensing apparatus in accordance with claim 9, wherein at least one portion is disposed at the connection ring that is configured to cause frictional engagement between the body and the connection ring to establish the pre-mounting.

12. The dispensing apparatus in accordance with claim 11, wherein the at least one portion is a prevention device configured to prevent the first and second inlets of the body from being axially moved in a direction opposite to an insertion direction.

13. The dispensing apparatus in accordance with claim 1, wherein the connection between the dispensing apparatus and the two-component cartridge is caused by at least one of a latching to and a rotation of the dispensing apparatus relative to the two-component cartridge.

14. The dispensing apparatus in accordance with claim 1, wherein the pre-mounted connection ring is non-releasably connected to the body following a rotation of the connection ring relative to the body, or the non-releasable connection between the pre-mounted connection ring and the body is caused by an axial displacement of the connection ring in a direction disposed opposite of the first and second outlets and by a rotation of the connection ring relative to the body.

15. The dispensing apparatus in accordance with claim 1, wherein the connection ring is configured to engage the body and the two-component cartridge, and the engagement at the body is at a shoulder of the body.

16. The dispensing apparatus in accordance with claim 15, wherein the connection ring is configured to engage the two-component cartridge after rotation relative to the body and the first and second inlets.

17. The dispensing apparatus in accordance with claim 15, wherein a connection between the connection ring and the two-component cartridge is configured to be caused by respective bayonet attachment device connecting the connection ring and the body to the two-component cartridge.

18. The dispensing apparatus in accordance with claim 15, wherein the body further comprises a locking device to lock the connection ring to the body once a connection between the connection ring and the two-component cartridge has been established to form a non-releasable connection.

19. The dispensing apparatus in accordance with claim 18, wherein the locking device includes elastic arms configured to engage into respective recesses disposed at the connection ring.

20. The dispensing apparatus in accordance with claim 1, wherein the dispensing apparatus extends a length of the first and second outlets of the cartridge, when mounted at the cartridge.

21. A dispensing system comprising:
a dispensing apparatus comprising a body, first and second inlets for flowable masses and first and second outlets through which the flowable masses are capable of being dispensed, with the first inlet being connected to the first outlet and the second inlet being connected to the second outlet through the body, the first and second inlets being spaced apart from one another by a first spacing and the first and second outlets being spaced apart from one another by a second spacing, the second spacing being larger than the first spacing, and a connection ring configured to engage the body and being pre-mounted at the body, the first outlet defining a first outer surface and the second outlet defining a second outer surface, the first and second outer surfaces at least partially facing each other and being spaced from each other so as to form a gap therebetween, the dispensing apparatus being configured to be non-releasably connected to a two-component cartridge via the connection ring for supply of the flowable masses to the first and second inlets; and
a two-component cartridge, with each cartridge of the two-component cartridge being capable of being filled with separate flowable masses.

22. A method of dispensing flowable masses, the method comprising:
providing a dispensing system comprising a dispensing apparatus including a body, first and second inlets for flowable masses and first and second outlets through which the flowable masses are capable of being dispensed, with the first inlet being connected to the first outlet and the second inlet being connected to the second outlet through the body, the first and second inlets being spaced apart from one another by a first spacing and the first and second outlets being spaced apart from one another by a second spacing, the second spacing being larger than the first spacing, and a connection ring configured to engage the body and being pre-mounted at the body, the first outlet defining a first outer surface and the second outlet defining a second outer surface, the first and second outer surfaces at least partially facing each other and being spaced from each other so as to form a gap therebetween, the dispensing apparatus being configured to be non-releasably connected to a two-component cartridge via the connection ring for supply of the flowable masses to the first and second inlets, and a two-component cartridge, with each cartridge of the two-component cartridge being capable of being separate flowable masses;

dispensing the flowable masses from the dispensing system; and a subsequent mixing of the flowable masses by hand.

* * * * *